United States Patent
Lim et al.

(10) Patent No.: US 9,203,031 B2
(45) Date of Patent: Dec. 1, 2015

(54) ORGANIC LIGHT EMITTING DISPLAY DEVICES AND METHODS OF MANUFACTURING ORGANIC LIGHT EMITTING DISPLAY DEVICES

(75) Inventors: Jin-O Lim, Yongin-si (KR); Seok-Hwan Hwang, Yongin-si (KR); Young-Kook Kim, Yongin-si (KR); Hye-Jin Jung, Yongin-si (KR); Sang-Hyun Han, Yongin-si (KR); Jong-Hyuk Lee, Yongin-si (KR)

(73) Assignee: Samsung Display Co., Ltd., Giheung-Gu, Yongin-si, Gyeonggi-Do (KR)

( * ) Notice: Subject to any disclaimer, the term of this patent is extended or adjusted under 35 U.S.C. 154(b) by 643 days.

(21) Appl. No.: 13/431,634

(22) Filed: Mar. 27, 2012

(65) Prior Publication Data
US 2013/0001530 A1    Jan. 3, 2013

(30) Foreign Application Priority Data
Jun. 28, 2011    (KR) .................. 10-2011-0062893

(51) Int. Cl.
| *H01L 51/54* | (2006.01) |
| *H01L 51/00* | (2006.01) |
| *C07C 13/70* | (2006.01) |
| *B82Y 10/00* | (2011.01) |
| *H01L 51/50* | (2006.01) |

(52) U.S. Cl.
CPC ............ *H01L 51/0052* (2013.01); *B82Y 10/00* (2013.01); *C07C 13/70* (2013.01); *H01L51/0045* (2013.01); *H01L 51/0072* (2013.01); *C07C 2103/90* (2013.01); *H01L 51/0081* (2013.01); *H01L 51/0085* (2013.01); *H01L 51/5016* (2013.01)

(58) Field of Classification Search
CPC ............ H01L 51/0045; H01L 51/0052; H01L 51/0072; H01L 51/0085; H01L 51/5016; H01L 51/0081; C07C 13/70; C07C 2103/90
See application file for complete search history.

(56) References Cited

U.S. PATENT DOCUMENTS

| 4,622,414 A | 11/1986 | McKervey |
| 4,882,449 A | 11/1989 | Harris |

(Continued)

FOREIGN PATENT DOCUMENTS

| JP | 2003-313546 | * 11/2003 |
| JP | 2007-335638 | * 12/2007 |

(Continued)

OTHER PUBLICATIONS

Translation for JP 2007-335638 (publication date Dec. 2007).*

*Primary Examiner* — Dawn L. Garrett
(74) *Attorney, Agent, or Firm* — Robert E. Bushnell, Esq.

(57) ABSTRACT

An organic light emitting display device comprising a first electrode; a hole transport layer, an emitting layer and an electron transport layer disposed sequentially on the first electrode; and a second electrode formed on the electron transport layer, wherein the emitting layer comprises a host material comprising a calixarene compound represented by Chemical Formula (1)

Chemical Formula (1)

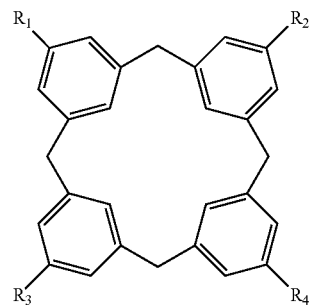

wherein, in the Chemical Formula (1), each of $R_1$ to $R_4$ is defined as in the specification.

15 Claims, 3 Drawing Sheets

(56) References Cited

U.S. PATENT DOCUMENTS

| | | | |
|---|---|---|---|
| 6,271,337 | B1 | 8/2001 | Lamartine et al. |
| 7,705,189 | B2 | 4/2010 | Nishikubo et al. |
| 2003/0232216 | A1* | 12/2003 | Saitoh et al. .................. 428/690 |
| 2009/0081357 | A1* | 3/2009 | Taka et al. ....................... 427/66 |

FOREIGN PATENT DOCUMENTS

| | | |
|---|---|---|
| KR | 1020070090504 A | 9/2007 |
| KR | 1020070119218 A | 12/2007 |
| WO | 2004039483 | 5/2004 |

* cited by examiner

ORGANIC LIGHT EMITTING DISPLAY DEVICES AND METHODS OF MANUFACTURING ORGANIC LIGHT EMITTING DISPLAY DEVICES

CROSS-REFERENCE TO RELATED APPLICATIONS

This application makes reference to, incorporates the same herein, and claims all benefits accruing under 35 U.S.C. §119 from an application for ORGANIC LIGHT EMITTING DISPLAY DEVICES AND METHODS OF MANUFACTURING THE ORGANIC LIGHT EMITTING DISPLAY DEVICES earlier filed in the Korean Intellectual Property Office on 28 Jun. 2011 and there duly assigned Serial No. 10-2011-0062893.

BACKGROUND OF THE INVENTION

1. Field of the Invention

The present invention relates to an organic light emitting display device and a method of manufacturing the organic light emitting display device. More particularly, the present invention relates to an organic light emitting display device having an improved luminance efficiency and a method of manufacturing the organic light emitting display device.

2. Description of the Related Art

An organic light emitting display (OLED) device may display desired information such as images, letters and/or characters using light generated by a combination of holes provided from an anode and electrons provided from a cathode in an organic layer thereof.

Conventionally, the organic layer in an OLED device may include a hole transport layer, an emitting layer, an electron transport layer, etc. Excitions may be generated in the emitting layer by a recombination of holes and electrons penetrating the hole transport layer and the electron transport layer, respectively. The energy level of the excitions may be lowered to a ground state, thereby to produce energy, and then a light having a wavelength that corresponds to the energy may be generated. The emitting layer may include a host material for generating the excitions and further include a dopant material, if necessary. To achieve high luminance efficiency or quantum efficiency, the energy needs to be easily transferred from the host material to the dopant material. Additionally, the host material needs to be selected from materials having good resistivity or durability against heat, electricity or mechanical stress in order to extend life-time of the organic light emitting display device.

SUMMARY OF THE INVENTION

The present invention provides an organic light emitting display device having improved luminance efficiency and improved electrical or mechanical characteristics.

The present invention provides a method of manufacturing an organic light emitting display device having improved luminance efficiency and improved electrical or mechanical characteristics.

According to an aspect of the present invention, there is provided an organic light emitting display device including a first electrode, a hole transport layer, an emitting layer, an electron transport layer and a second electrode. The hole transport layer, the emitting layer and the electron transport layer may be disposed sequentially on the first electrode. The second electrode may be disposed on the electron transport layer. The emitting layer may include a host material comprising a calixarene compound represented by the following Chemical Formula (1) and a dopant material.

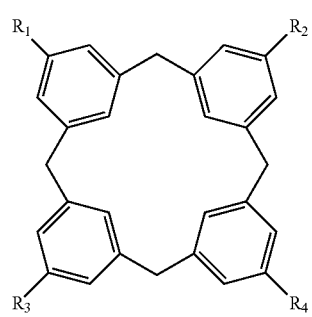

Chemical Formula (1)

In the above Chemical Formula (1), each of $R_1$ to $R_4$ may independently represent hydrogen, deuterium, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a unsubstituted $C_6$-$C_{60}$ aryl group, a $C_6$-$C_{60}$ aryl group substituted with an aryl group, a $C_6$-$C_{60}$ aryl group substituted with a polyaromatic group, a $C_5$-$C_{50}$ amino group substituted with an aryl group, a $C_4$-$C_{60}$ unsubstituted heteroaryl group, a $C_4$-$C_{60}$ heteroaryl group substituted with an aryl group, a $C_6$-$C_{60}$ unsubstituted and condensed polyaromatic group, a $C_6$-$C_{60}$ unsubstituted and non-condensed polyaromatic group, a $C_6$-$C_{60}$ condensed polyaromatic group substituted with an aromatic group, a $C_6$-$C_{60}$ non-condensed polyaromatic group substituted with an aromatic group, a cyano group, a nitro group, a hydroxyl group or a carboxylic group.

In some embodiments, each of $R_1$ to $R_4$ in the Chemical Formula (1) may independently represents one selected from the group consisting of a phenyl group, a biphenyl group, a naphthyl group, an anthracene group, a phenanthrene group, a pyrene group or a benzopyrene group which are unsubstituted or substituted with an aromatic group.

In some embodiments, the host material may includes at least one calixarene compound selected from the compounds represented by the following Chemical Formula (2), Chemical Formula (3), Chemical Formula (4) or Chemical Formula (5).

Chemical Formula (2)
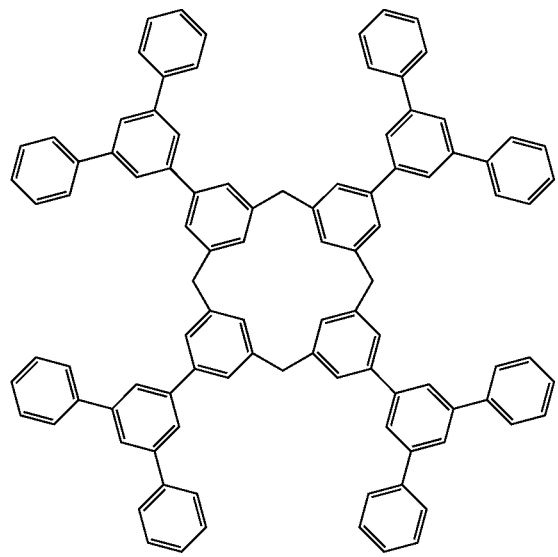
Chemical Formula (3)
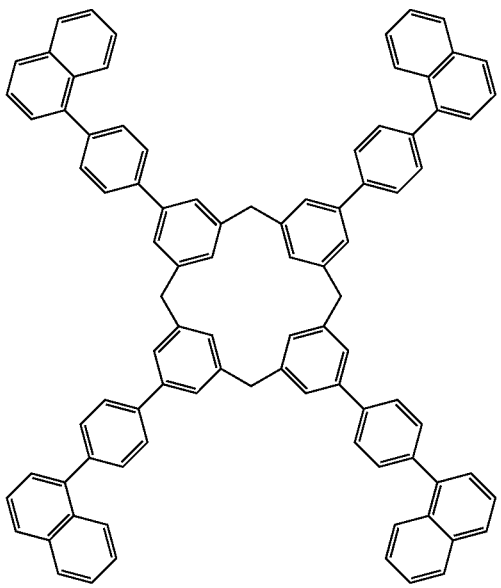
Chemical Formula (4)
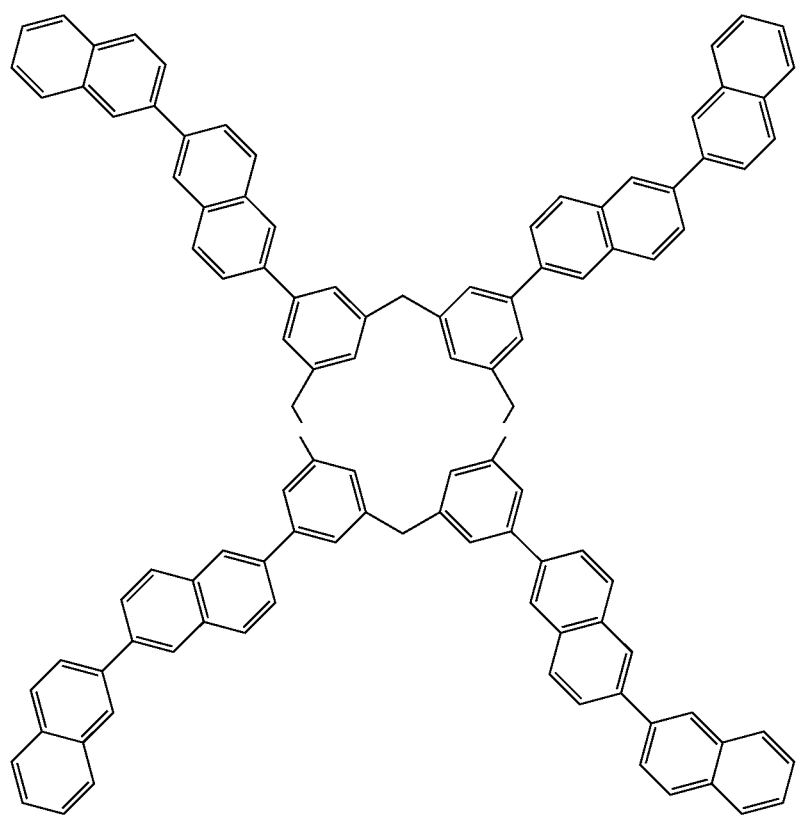

Chemical Formula (5)
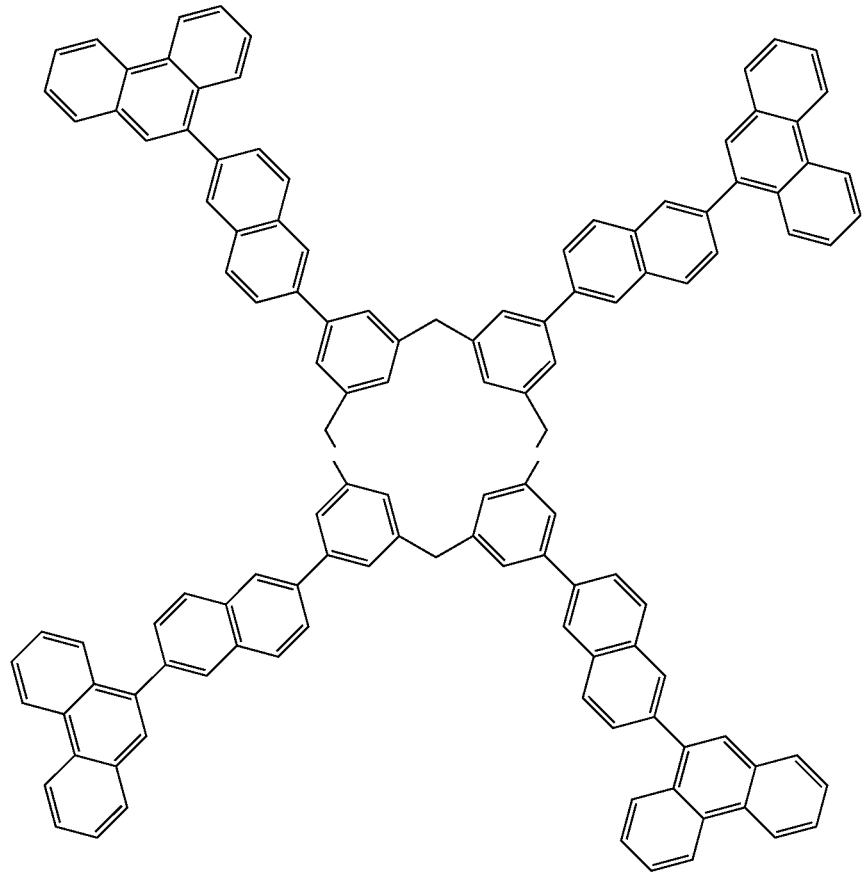

In some embodiments, each of $R_1$ to $R_4$ in the Chemical Formula (1) may independently represent an indole group or an indole group substituted with an aryl group. In this case, the host material may include a calixarene compound represented by the following Chemical Formula (6).

Chemical Formula (6)

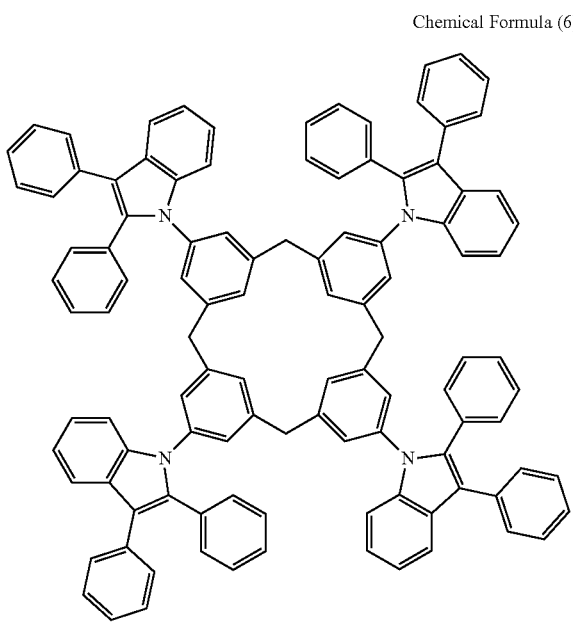 [SMILES: c1ccc(-c2c(-c3ccccc3)n(-c3cc4cc(c3)Cc3cc(cc(-n5c(-c6ccccc6)c(-c6ccccc6)c6ccccc65)c3)Cc3cc(cc(-n5c(-c6ccccc6)c(-c6ccccc6)c6ccccc65)c3)Cc3cc(cc(-n5c(-c6ccccc6)c(-c6ccccc6)c6ccccc65)c3)C4)c3ccccc23)cc1]

In some embodiments, the host material may include at least one calixarene compound selected from the compounds represented by the following Chemical Formula (7), Chemical Formula (8) or Chemical Formula (9).

Chemical Formula (7)

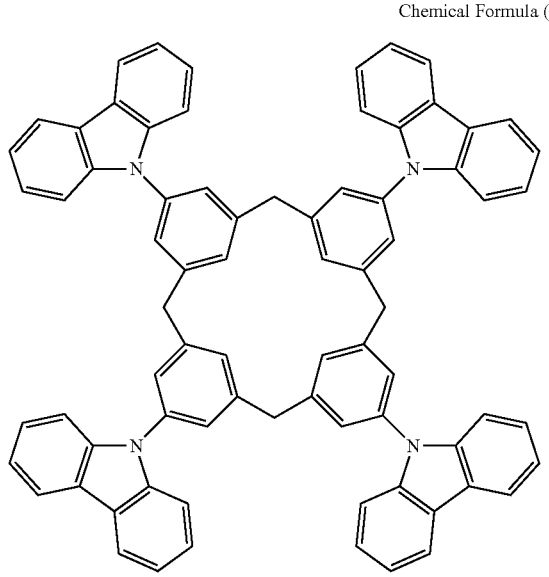

Chemical Formula (8)

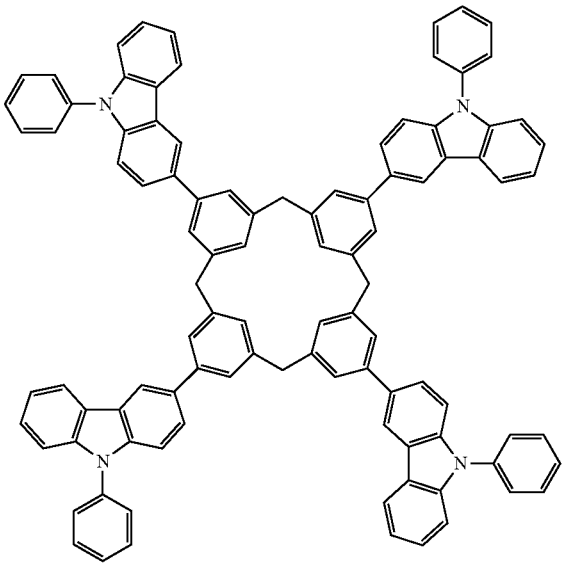

Chemical Formula (9)

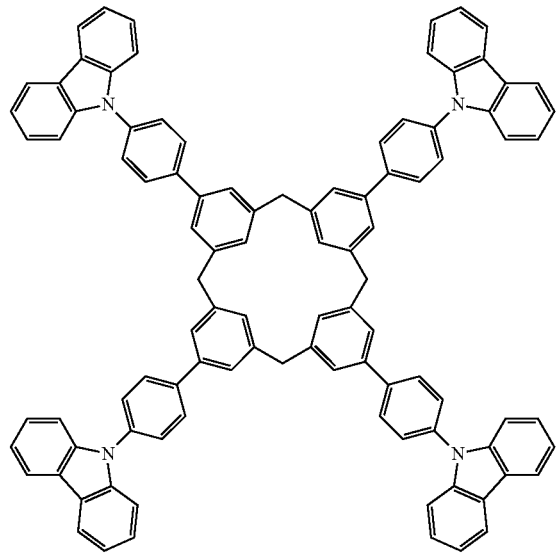

In some embodiments, the dopant material may include at least one organometallic compound having a metal selected from the group consisting of iridium (Ir), platinum (Pt), osmium (Os) or gold (Au). For example, the dopant material may include PtOEP, Ir(ppy)3 or iridium (III) bis[2-(2'-benzothienyl)pyridinato-N,C3'](acetylacetonate) (BTPIr).

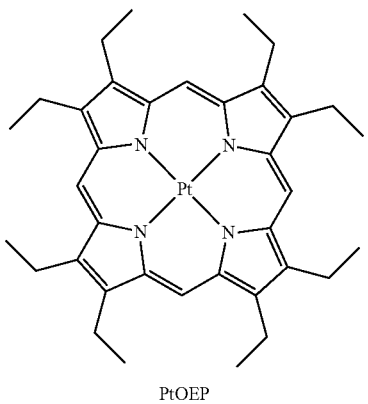

PtOEP

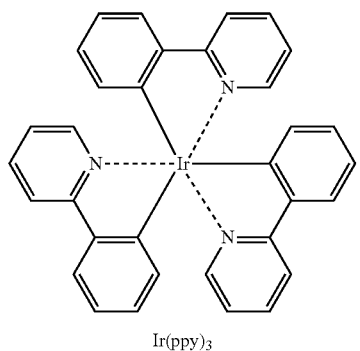

Ir(ppy)₃

In some embodiments, a hole injection layer may be further disposed between the first electrode and the hole transport layer. An electron injection layer may be also disposed between the electron transport layer and the second electrode.

In some embodiments, a hole blocking layer may be further disposed between the emitting layer and the electron transport layer. An electron blocking layer may be also disposed between the emitting layer and the hole transport layer.

In some embodiments, the organic light emitting display device may further include switching device electrically connected to the first electrode. The first electrode may be electrically connected to an electrode of the switching device to serve as an anode providing holes.

In some embodiments, the host material may include a fluorescent host material or a phosphorescent host material and the dopant material may include a fluorescent dopant material or a phosphorescent dopant material.

According to another aspect of the present invention, there is provided a method of manufacturing an organic light emitting display device. In the method, a substrate may be formed with a switching device; and a first electrode may be formed on the substrate. A hole transport layer, an emitting layer and an electron transport layer may be formed sequentially on the first electrode. A second electrode may be formed on the electron transport layer. The emitting layer may be formed using a host material comprising a calixarene compound represented by the following Chemical Formula (1) and a dopant material.

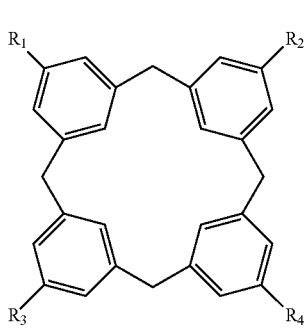

Chemical Formula (1)

In the above Chemical Formula (1), each of $R_1$ to $R_4$ may independently represent hydrogen, deuterium, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a unsubstituted $C_6$-$C_{60}$ aryl group, a $C_6$-$C_{60}$ aryl group substituted with an aryl group, a $C_6$-$C_{60}$ aryl group substituted with a polyaromatic group, a $C_5$-$C_{50}$ amino group substituted with an aryl group, a $C_4$-$C_{60}$ unsubstituted heteroaryl group, a $C_4$-$C_{60}$ heteroaryl group substituted with an aryl group, a $C_6$-$C_{60}$ unsubstituted and condensed polyaromatic group, a $C_6$-$C_{60}$ unsubstituted and non-condensed polyaromatic group, a $C_6$-$C_{60}$ condensed polyaromatic group substituted with an aromatic group, a $C_6$-$C_{60}$ non-condensed polyaromatic group substituted with an aromatic group, a cyano group, a nitro group, a hydroxyl group or a carboxylic group.

In some embodiments, each of $R_1$ to $R_4$ in the Chemical Formula (1) may independently represent one selected from the group consisting of a phenyl group, a biphenyl group, a naphthyl group, an anthracene group, a phenanthrene group, a pyrene group or a benzopyrene group which are unsubstituted or substituted with an aromatic group.

In some embodiments, each of $R_1$ to $R_4$ in the Chemical Formula (1) may independently represent an indole group or an indole group substituted with an aryl group.

In some embodiments, a hole injecting layer may be further formed on the first electrode prior to forming the hole transport layer. An electron injecting layer may be also formed on the electron transport layer prior to forming the second electrode.

In some embodiments, an electron blocking layer may be further formed on the hole transport layer prior to forming the emitting layer. A hole blocking layer may be formed on the emitting layer after forming the emitting layer.

According to some embodiments, the organic light emitting display device may include an emitting layer having calixarene compounds as fluorescent or phosphorescent host materials. The calixarene compounds may have a high glass transition temperature and a high melting point, thereby to have good resistivity against the heat generated in electrodes and organic layers. Thus, the organic light emitting display device containing the calixarene compounds may have an extended life-time and enhanced durability. Further, the calixarene compounds may have high luminance efficiency or quantum efficiency so that fluorescent or phosphorescent characteristics of the emitting layer may be improved. Consequently, the brightness of the organic light emitting display device may be increased.

BRIEF DESCRIPTION OF THE DRAWINGS

A more complete appreciation of the present invention, and many of the attendant advantages thereof, will be readily apparent as the present invention becomes better understood by reference to the following detailed description when considered in conjunction with the accompanying drawings in which like reference symbols indicate the same or similar components.

FIG. 1 is a schematic cross-sectional view of an organic light emitting display device in accordance with an embodiment of the present invention;

FIG. 2 is a schematic cross-sectional view of an organic light emitting display device in accordance with another embodiment of the present invention;

FIG. 3 is a schematic cross-sectional view of an organic light emitting display device in accordance with another embodiment of the present invention;

FIG. 4 is a schematic cross-sectional view of an organic light emitting display device in accordance with another embodiment of the present invention; and FIG. 5 is a schematic cross-sectional view of an organic light emitting display device in accordance with another embodiment of the present invention.

DETAILED DESCRIPTION OF THE INVENTION

Figure 1:
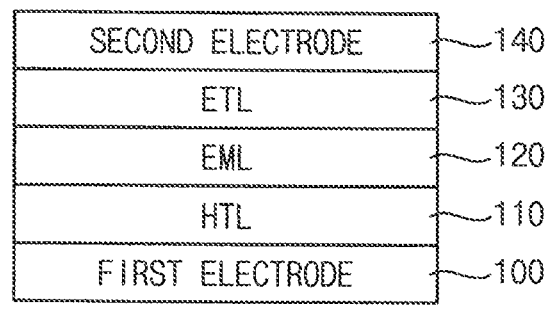
FIGS. 1 to 5 represent, non-limiting, example embodiments as described herein.

The present invention will be described more fully hereinafter with reference to the accompanying drawings, in which some example embodiments of the present invention are shown. The present invention may, however, be embodied in many different forms and should not be construed as limited to the example embodiments set forth herein. Rather, these example embodiments are provided so that this description will be thorough and complete, and will fully convey the scope of the present invention to those skilled in the art. In the drawings, the sizes and relative sizes of layers and regions may be exaggerated for clarity.

It will be understood that when an element or layer is referred to as being "on" "connected to" or "coupled to" another element or layer, it can be directly on, connected or coupled to the other element or layer or intervening elements or layers may be present. In contrast, when an element is referred to as being "directly on" "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, components, and/or groups but do not preclude the presence or addition of one or more other features, integers, steps, operations, elements, components, and/or groups thereof.

Example embodiments of the present invention are described herein with reference to schematic cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures of the present invention are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic cross-sectional view of an organic light emitting display (OLED) device in accordance with an embodiment of the present invention.

Referring to FIG. 1, an OLED device may include a first electrode 110 and a second electrode 140. The OLED device may also include a hole transport layer (HTL) 110, an emitting layer (EML) 120 and an electron transport layer (ETL) 130 sequentially stacked on the first electrode 100 between the first and the second electrodes 100 and 140.

Figure 2:
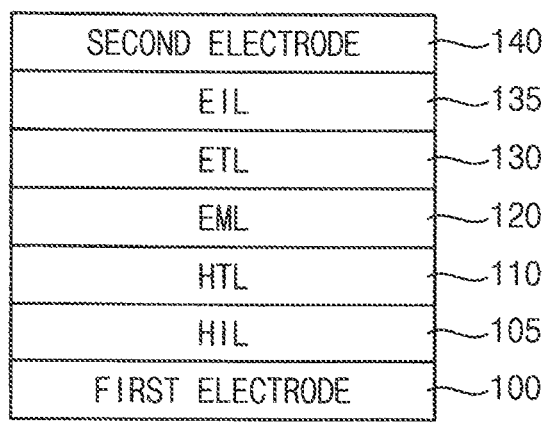

FIG. 2 is a schematic cross-sectional view of an OLED device in accordance with another embodiment of the present invention.

As illustrated in FIG. 2, an OLED device may further include an hole injection layer (HIL) 105 formed between the first electrode 100 and the HTL 110, and an electron injection layer (EIL) 135 formed between the second electrode 140 and the ETL 130 in comparison to the OLED device illustrated in FIG. 1.

Figure 3:
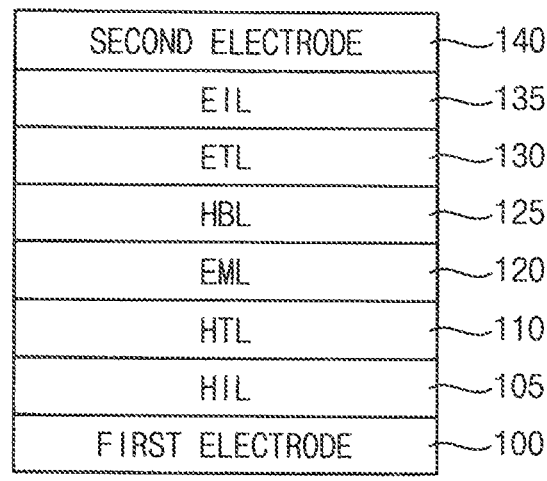

FIG. 3 is a schematic cross-sectional view of an OLED device in accordance with another embodiment of the present invention.

As illustrated in FIG. 3, an OLED device may further include a hole blocking layer (HBL) 125 formed between the EML 120 and the ETL 130 in comparison to the OLED device illustrated in FIG. 2.

Figure 4:
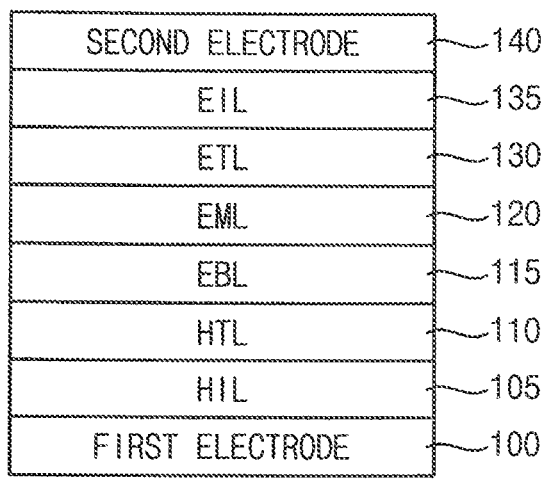

FIG. 4 is a schematic cross-sectional view of an OLED device in accordance with another embodiment of the present invention.

As illustrated in FIG. 4, an OLED device may further include an electron blocking layer (EBL) 115 formed between the EML 120 and the HTL 110 in comparison to the OLED device illustrated in FIG. 3.

Figure 5:
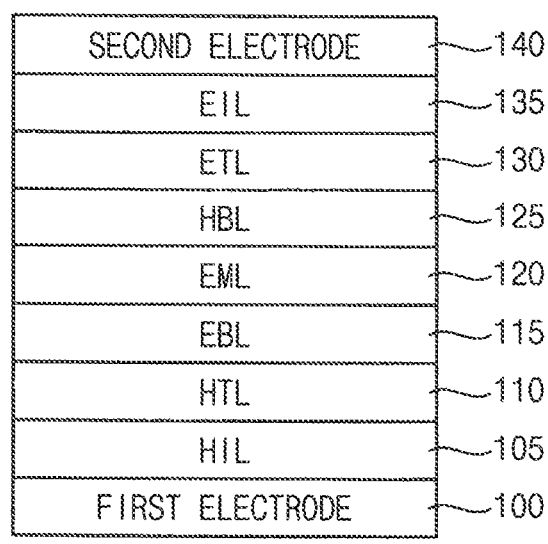

FIG. 5 is a schematic cross-sectional view of an OLED device in accordance with another embodiment of the present invention.

As illustrated in FIG. 5, an OLED device may further include the HBL 125 formed between the EML 120 and the ETL 130 and the EBL 115 formed between the EML 120 and the HTL 110 in comparison to the OLED device illustrated in FIG. 2.

As for the OLED devices illustrated in FIGS. 1 to 5, the first electrode 100 may serve as an anode for providing the HTL 110 with holes and the second electrode 140 may serve as a cathode for providing the ETL 130 with electrons.

The first electrode 100 may include transparent metal oxide having a relatively high work function and a good electrical conductivity. For example, the first electrode 100 may include indium tin oxide (ITO), indium zinc oxide (IZO), zinc oxide (ZnOx), gallium oxide (GaOx), and tin oxide (SnOx), etc. These oxides may be used alone or in a combination thereof. The first electrode 100 may have a single-layered structure or a multi-layered structure including a metal oxide film.

The second electrode 140 may include a metal having a relatively low work function. For example, the second electrode 140 may include lithium (Li), magnesium (Mg), aluminium (Al), silver (Ag) or alloys thereof, etc. The second electrode 140 may have a single-layered structure or a multi-layered structure including a metal film and/or an alloy film.

The HIL 105 may facilitate hole injection from the first electrode 100 into the HTL 110. The HIL 105 may include, but is not limited to, 4,4',4"-tris(N-carbazolyl)-triphenylamine (TCTA), 4,4',4"-tris (3-methylphenylphenylamino) triphenylamine (m-MTDATA), 1,3,5-tris[4-(3-methylphenylphenylamino)phenyl]benzene (m-MTDAPB), 2-TNATA represented by the following Structural Formula (1) or mixtures of these materials.

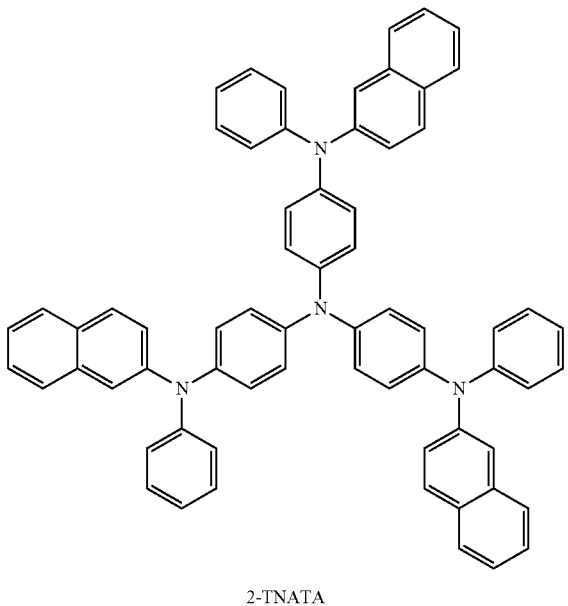

Structural Formula (1)

2-TNATA

The HTL 110 may include at least one hole-transporting material. The HTL 110 may include, but is not limited to, 4,4-bis[N-(1-naphtyl)-N-phenylamino]biphenyl (NPB) represented by the following Structural Formula (2), N,N-diphenyl-N,N-bis(3-methylphenyl)-1,1-biphenyl-4,4-diamine (TPD) represented by the following Structural Formula (3), (N,N-di-1-naphthyl-N,N-diphenyl-1,1-biphenyl-4,4-diamine (NPD), N-phenylcarbazole, polyvinylcarbazole or mixtures of these materials.

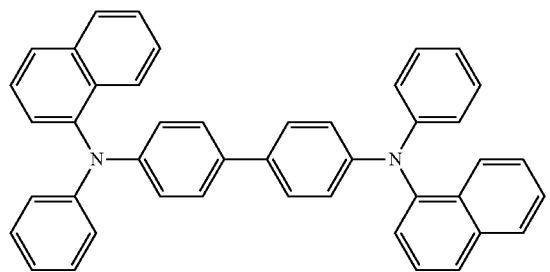

Structural Formula (2)

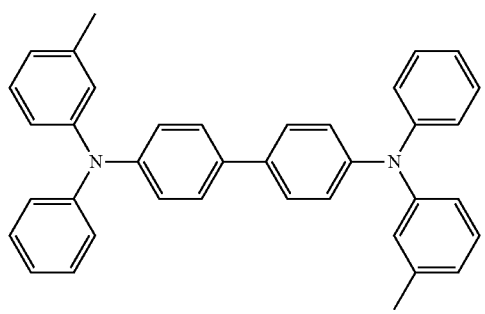

Structural Formula (3)

The HBL 125 may include materials having good electron-transporting and low hole-transporting characteristics. The HBL 125 may include, but is not limited to, bathocuproine (BCP), 3-(4-biphenylyl)-4-phenyl-5-(4-tert-butylphenyl)-1,2,4-triazole (TAZ), etc. These may be used alone or in a mixture thereof. In contrast, the EBL 115 may include materials having good hole-transporting and low electron-transporting characteristics. The EBL 115 may include, but is not limited to, Ir(ppz)$_3$ represented by the following Structural Formula (4).

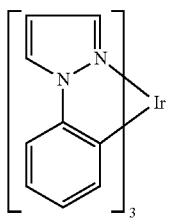

Structural Formula (4)

The ETL 130 may include at least one electron-transporting material such as tris(8-quinolinolate)aluminium (Alq), rubrene, etc.

The EIL 135 may include, e.g., LiF, NaCl, CsF, Li$_2$O, BaO, etc. These may be used alone or in a mixture thereof.

The EML 120 may include a phosphorescent or a fluorescent host material and a phosphorescent or a fluorescent dopant material.

Energy may be generated by phosphorescent or fluorescent mechanisms in the EML 120 and a light corresponding to the energy may be generated. According to the fluorescent mechanism, a singlet exciton may be transferred to a ground state to produce energy. According to the phosphorescent mechanism, a triplet exciton may be transferred to a ground state to produce energy. As for the phosphorescent mechanism, the triplet exciton may not be directly transferred to the ground state so that the triplet exciton may undergo an electron spin flipping to be transferred to the ground state. Thus, a light-emitting time by the phosphorescent mechanism may be longer than that by the fluorescent mechanism.

Suitable host materials for the EML 120 may be selected in order to improve luminance efficiency of the OLED device. The host material for the phosphorescent mechanism may have properties for the stable transfer of triplet energy to the dopant material and may have a relatively long life-time. Additionally, the host material may have good charge-transporting capability. Furthermore, the host material may have resistivity to a Joule heat produced between electrodes or between organic layers and electrodes during light-emission by a field effect, thereby to obtain electrical or mechanical stability.

Conventional host materials may include tris(8-hydroxyquinolate)aluminium (Alq3) or 4,4'-N,N'-dicarbazole-biphenyl (CBP) represented by the following Structural Formula (5).

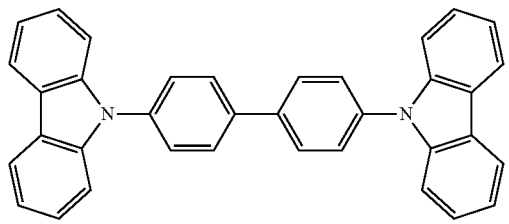

Structural Formula (5)

CBP

However, the conventional host material may have a low glass transition temperature (e.g. about 110° C. for CBP) and may be easily crystallized so that the host material may have a low thermal stability and a short life-time.

According to some embodiments of the present invention, the host material in the EML 120 may include a calixarene compound represented by the following Chemical Formula (1).

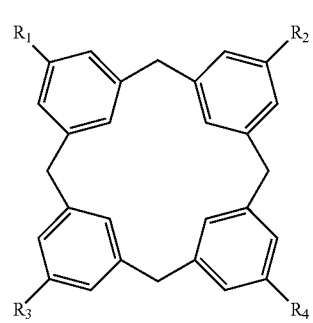

Chemical Formula (1)

In the above Chemical Formula (1), each of $R_1$ to $R_4$ may independently represent hydrogen, deuterium, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a unsubstituted $C_6$-$C_{60}$ aryl group, a $C_6$-$C_{60}$ aryl group substituted with an aryl group, a $C_6$-$C_{60}$ aryl group substituted with a polyaromatic group, a $C_5$-$C_{50}$ amino group substituted with an aryl group, a $C_4$-$C_{60}$ unsubstituted heteroaryl group, a $C_4$-$C_{60}$ heteroaryl group substituted with an aryl group, a $C_6$-$C_{60}$ unsubstituted and condensed polyaromatic group, a $C_6$-$C_{60}$ unsubstituted and non-condensed polyaromatic group, a $C_6$-$C_{60}$ condensed polyaromatic group substituted with an aromatic group, a $C_6$-$C_{60}$ non-condensed polyaromatic group substituted with an aromatic group, a cyano group, a nitro group, a hydroxyl group or a carboxylic group. The host material may include a plurality of compounds, each of which is represented by the above Chemical Formula (1).

In some embodiments of the present invention, each of $R_1$ to $R_4$ in the above Chemical Formula (1) may independently represent one selected from the group consisting of a phenyl group, a biphenyl group, a naphthyl group, an anthracene group, a phenanthrene group, a pyrene group or a benzopyrene group which are unsubstituted or substituted with an aromatic group.

In some embodiments of the present invention, each of $R_1$ to $R_4$ in the above Chemical Formula (1) may independently represent a heteroaryl group such as an indole group. The heteroaryl group may be unsubstituted or substituted with an aryl group.

Non-limiting examples of the calixarene compound represented by the above Chemical Formula (1) may be illustrated below. Each of the compounds is numbered for convenience of reference.

Examples of Calixarene Compounds
1
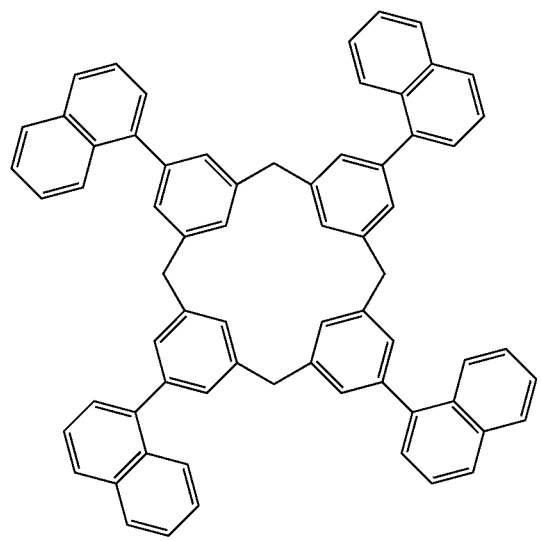
2
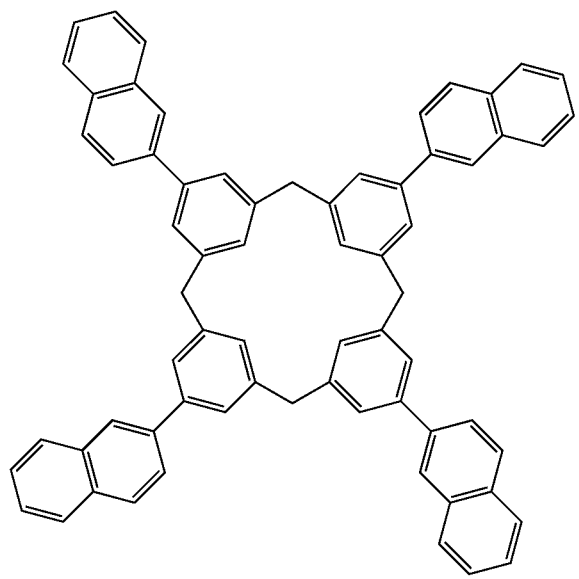
3
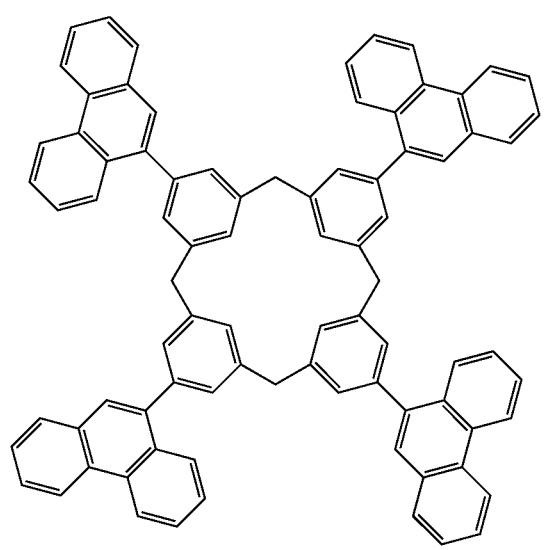
4
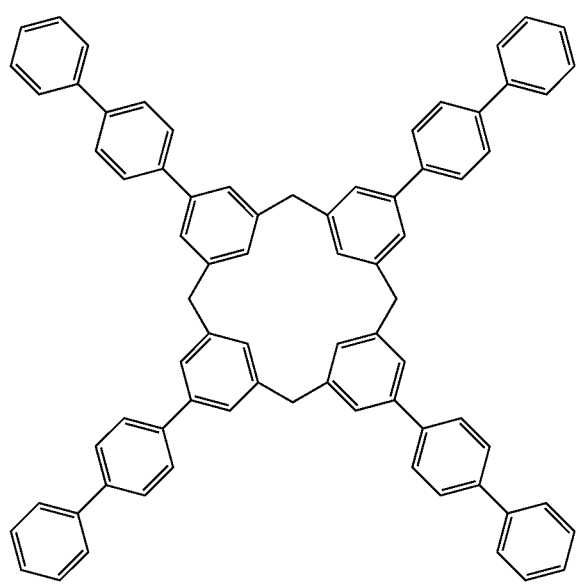

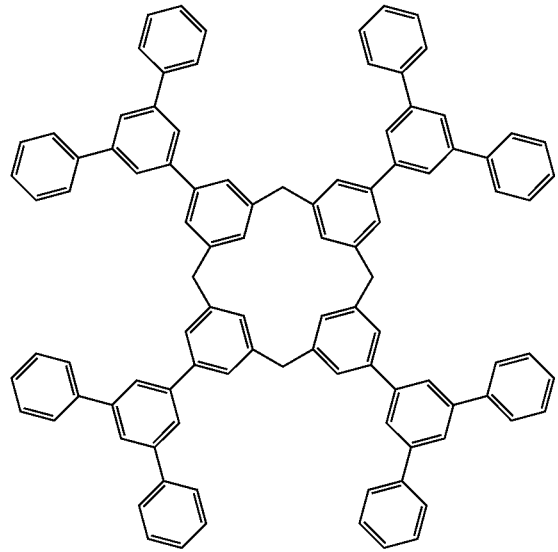
5
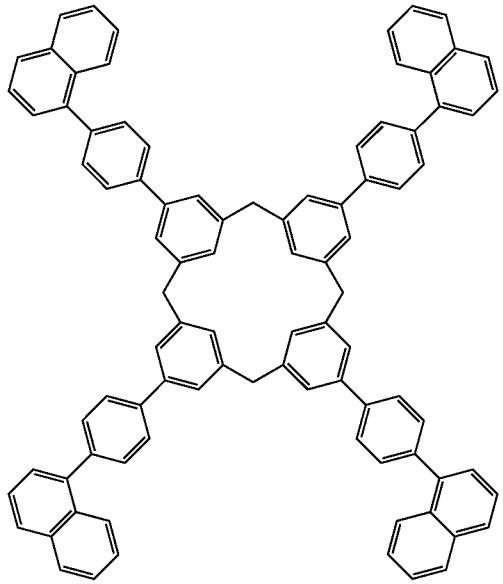
6
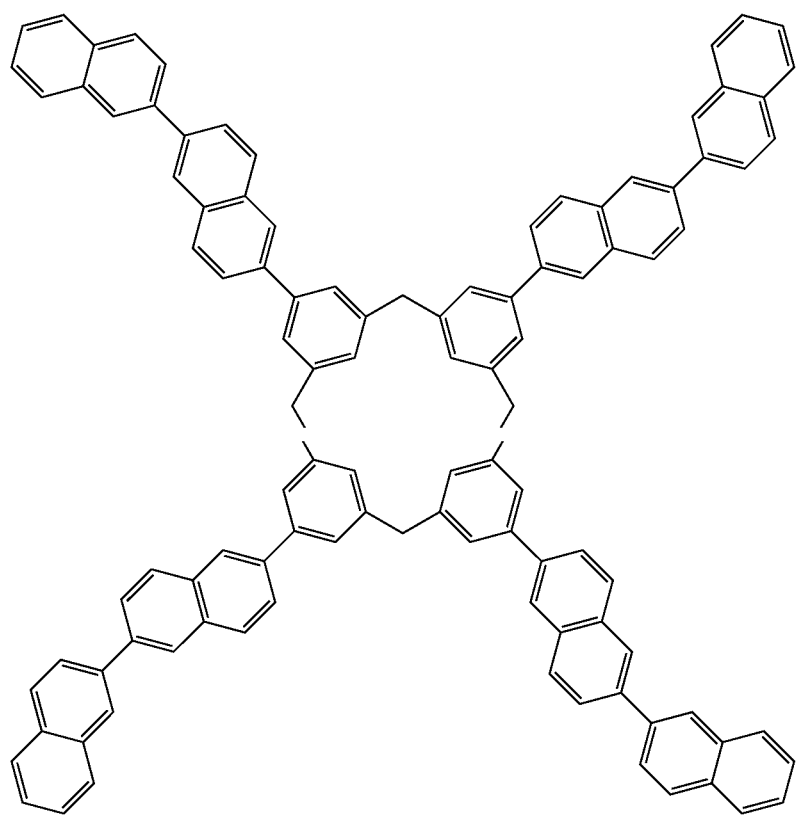
7

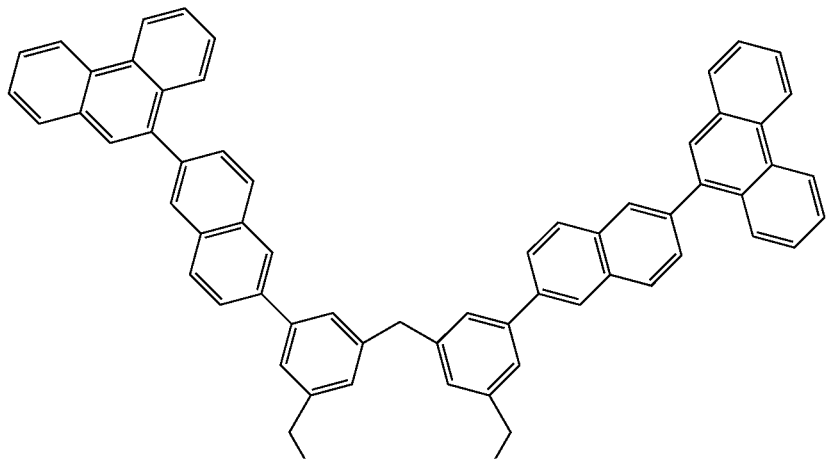

-continued
11
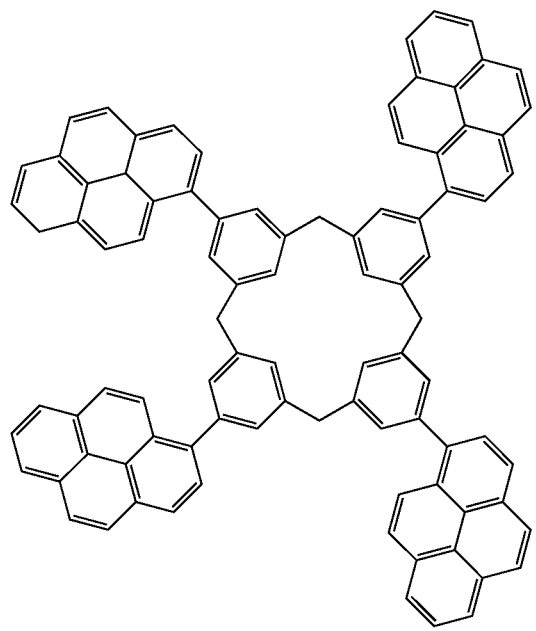
12
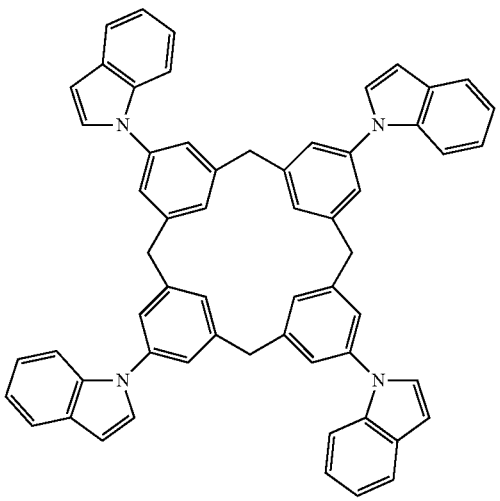
13
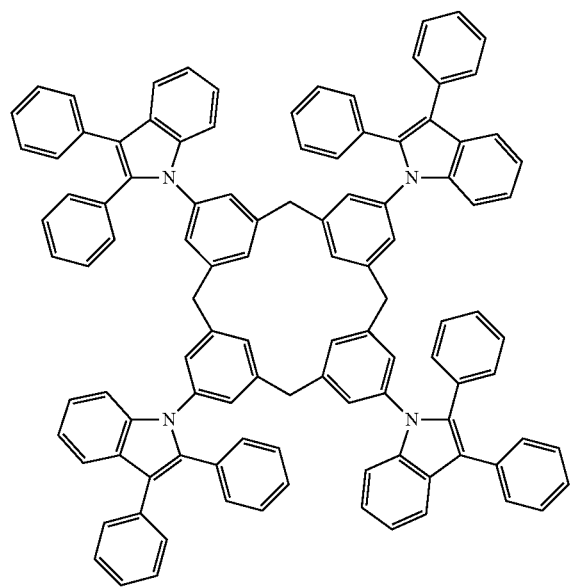
14
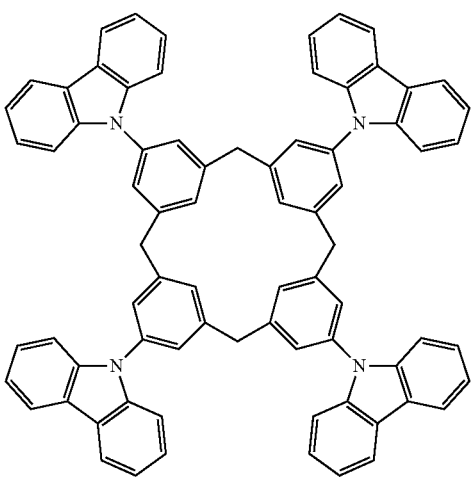

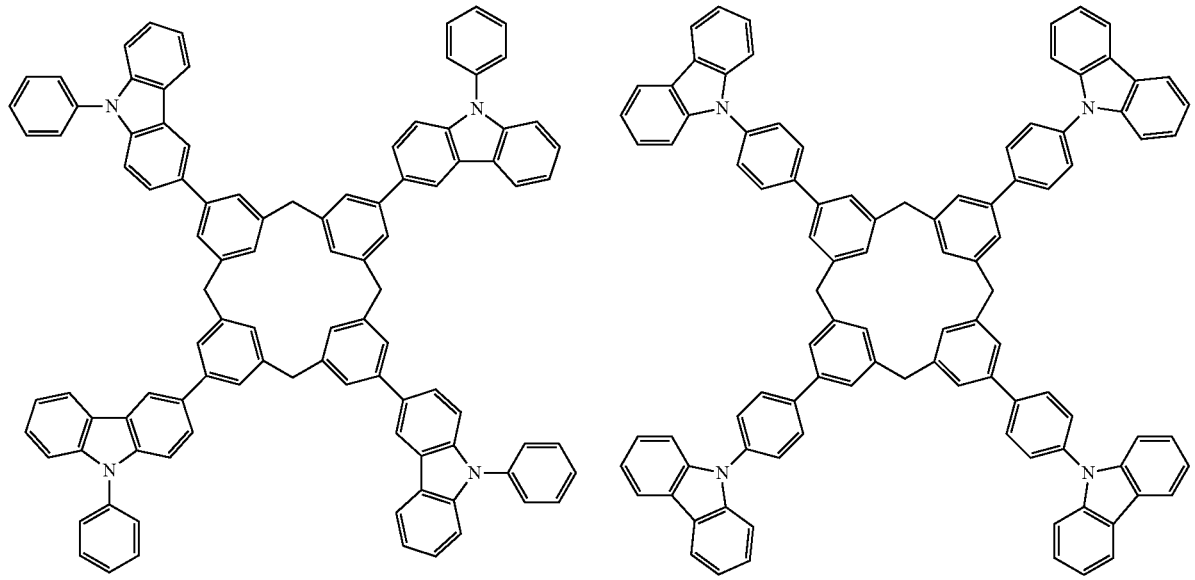

In some embodiments of the present invention, each of $R_1$ to $R_4$ may independently represent an aryl group, a polycyclic aromatic group and a heteroaryl group which are unsubstituted. In some embodiments of the present invention, each of $R_1$ to $R_4$ may also independently represent an aryl group, a polycyclic aromatic group and a heteroaryl group which are substituted by other aromatic groups. The calixarene compound used in the EML 120 layer of the present invention may have excellent thermal, electrical and mechanical stability. Specifically, the calixarene compound used in the EML 120 layer of the present invention may have a high glass transition temperature and a high melting point together with suitable charge-transporting capability. Thus, the calixarene compound used in the EML 120 layer of the present invention may have the resistivity against the Joule heat generated during a light-emission by a field effect. Therefore, the OLED device employing the calixarene compound may have improved durability and high luminance efficiency.

The dopant material in the EML 120 of the present invention may include phosphorescent or fluorescent dopants. The dopant material may include at least one organometallic compound having a metal selected from the group consisting of platinum (Pt), Iridium (Ir), osmium (Os), gold (Au), etc. in other embodiments of the present invention, the dopant material may include a phosphorescent dopant such as PtOEP, Ir(ppy)$_3$, BTPIr, etc. These may be used alone or in a mixture thereof. Ir(ppy)$_3$ and BTPIr are represented by the following Structural Formula (6) and Structural Formula (7), respectively.

Structure Formula (6)

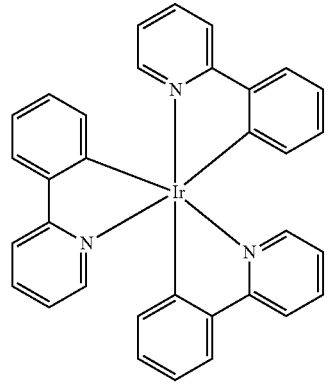

Structure Formula (7)

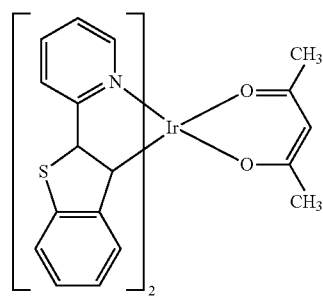

Exemplary synthetic examples of the calixarene compounds are illustrated, hereinafter.

Synthetic Example 1

Synthesis of Compound 8

Intermediate E was synthesized through a reaction path illustrated in the following Reaction Equation (1).

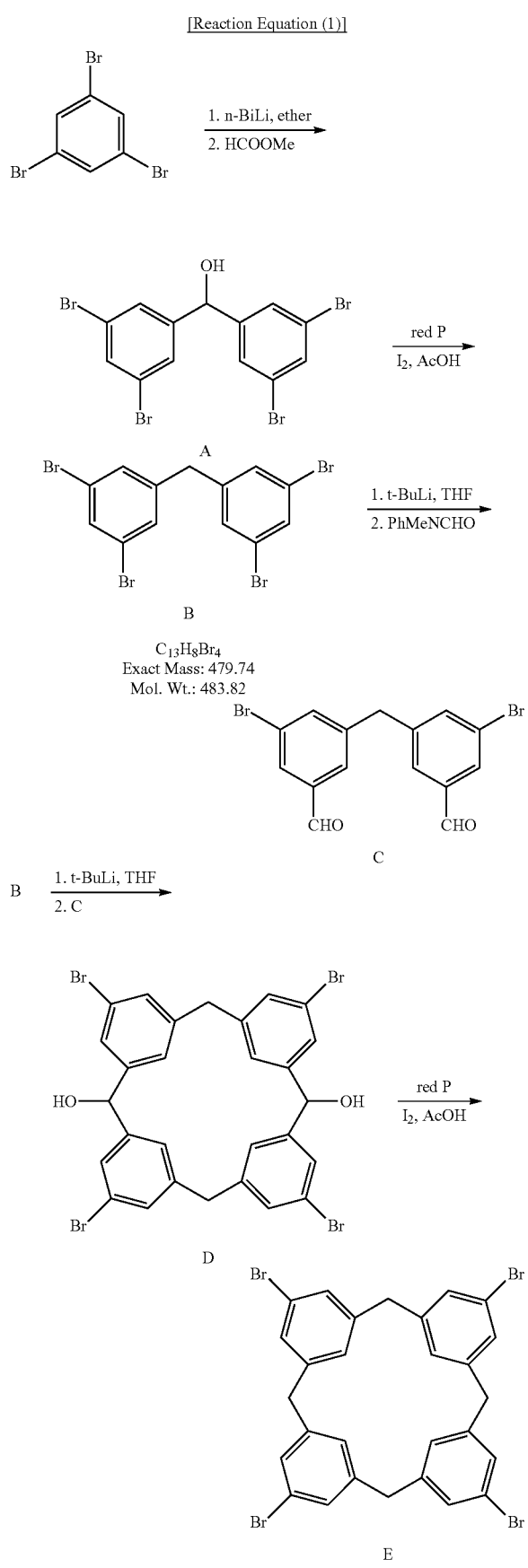

[Reaction Equation (1)]

I. Synthesis of Intermediate A 28.3 g (90 mmol) of 2,4,6-tribromotoluene was dissolved in 600 mL of diethylether and cooled to a point of −78° C. 36.0 mL (90 mmol, 2.5M in hexane) of n-butyl lithium was further added. The obtained solution was stirred for about 1 hour at −78° C. and 2.7 mL (44 mmol) of methylformate was added to the solution at the same temperature. The resultant mixture was stirred for 16 hours heating slowly to a room temperature and was washed by distilled water and diethylether. A washed dithylether layer was dried using $MgSO_4$ and further decompression-dried to obtain a coproduct. The coproduct was recrystallized in boiling hexane to obtain 19.3 g of Intermediate A as a colorless solid form (86% yields).

II. Synthesis of Intermediate B 72.8 g (146 mmol) of Intermediate A, 15.3 g (492 mmol) of red phosphorous (red P) and 7.41 g (29.2 mmol) of iodine were mixed and dissolved in 1,800 mL of acetic acid. The mixture was heated and refluxed for 42 hours. After completing the reaction, water was added to the mixture and a resultant precipitate was formed. The precipitate was filtered and washed using water and methanol. The precipitate was extracted by a soxhlet extraction process using chloroform to obtain 63 g of Intermediate B as a white solid form (89% yields).

III. Synthesis of Intermediate C 4.01 g (8.29 mmol) of Intermediate B was dissolved in 100 mL of tetrahydrofuran (THF) and cooled to a point of −78° C. 19.5 mL (33.2 mmol, 1.7M in pentane) of t-butyl lithium was slowly added. The obtained solution was stirred for about 1 hour at −78° C. and 10.4 mL (16.6 mmol, 1.6M in THF) of methylformanilide was added at the same temperature. The solution was stirred for 16 hours heating slowly to 0° C. The resultant solution was washed using distilled water and chloroform. The solution was recrystallized in chloroform and hexane to obtain 1.95 g of Intermediate C as a yellow solid form (yield 61%).

IV. Synthesis of Intermediates D and E 1.27 g (2.62 mmol) of Intermediate B was dissolved in 50 mL of THF and cooled to a point of −78° C. 6.15 mL (10.5 mmol, 1.7M in pentane) of t-butyl lithium was slowly added. The obtained solution was stirred for about 1 hour at −78° C. and 1.00 g (2.62 mmol) of Intermediate C dissolved in 50 mL of THF was added at the same temperature. The solution was stirred for 36 hours heating slowly to a room temperature and was extracted three times at a room temperature using distilled water and 50 mL of ethylacetate to obtain an organic layer. The organic layer was dried by magnesium sulfate to vaporize solvent. The resultant residue was recrystallized in chloroform and THF to obtain Intermediate D as a white solid form. 2.04 g of Intermediate D, 4.45 g (150 mmol) of red P and 1.08 g (4.2 mmol) of iodine were dissolved in 100 mL of acetic acid. The obtained solution was heated and refluxed for 48 hours. The solution was boiled to remove acetic acid and iodine. A remaining residue was washed by water and methanol, and extracted by a soxhlet extraction process using chloroform to obtain 0.83 g of Intermediate E as a white solid form (more than 40% yield).

V. Synthesis of Compound 8

Compound 8, which is one of Examples of Calixarene Compounds, was synthesized through a reaction path illustrated in the following Reaction Equation (2).

[Reaction Equation (2)]

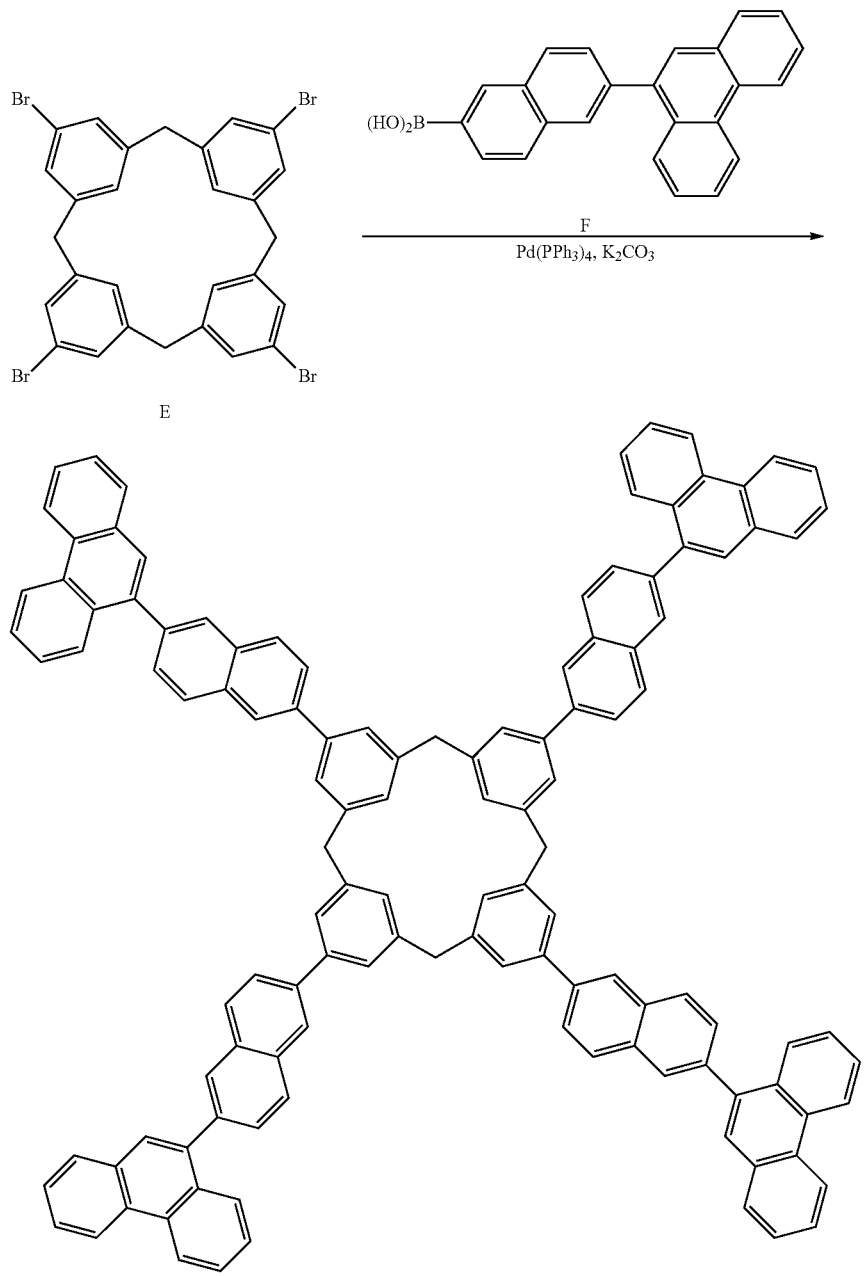

676 mg (1.0 mmol) of Intermediate E, 1.532 g (4.4 mmol) of Intermediate F, 50 mg (0.05 mmol) of Pd(PPh$_3$)$_4$, 415 mg (3.0 mmol) of K$_2$CO$_3$ were dissolved in 15 mL of toluene and stirred for 3 hours at 90° C. The obtained solution was cooled to a room temperature and extracted three times using distilled water and 20 mL of ethylacetate to obtain an organic layer. The organic layer was dried by magnesium sulfate to vaporize solvent. The resultant residue was separated and purified using a silica gel chromatography to obtain 659 mg of Compound 8 as a white solid form (42% yield). The resultant Compound 8 was detected using HR-MS. A measured value of Compound 8 was 1569.6260 [M+1] and a calculated value based on a chemical formula of Compound 8 (C$_{124}$H$_{80}$) is 1568.6260.

The resultant Compound 8 was also confirmed using $^1$H-NMR (CDCl$_3$, 300 MHz) to show following peaks represented by δ (ppm): 8.65-8.63 (m, 4H), 8.42-8.41 (m, 4H), 8.12 (s, 4H), 8.11 (s, 4H), 8.02 (s, 3H), 8.00 (s, 5H), 7.87-7.86 (m, 4H), 7.85 (d, 2H), 7.83 (d, 2H), 7.81-7.77 (m, 4H), 7.73 (d, 2H), 7.71 (d, 2H), 7.69-7.61 (m, 8H), 7.54-7.50 (t, 6H), 7.32 (s, 10H), 7.15-7.11 (t, 4H), 6.60 (m, 4H), 4.03 (s, 8H).

Synthetic Example 2

Synthesis of Compound 13

Compound 13, which is one of Examples of Calixarene Compounds, was synthesized through a reaction path illustrated in the following Reaction Equation (3).

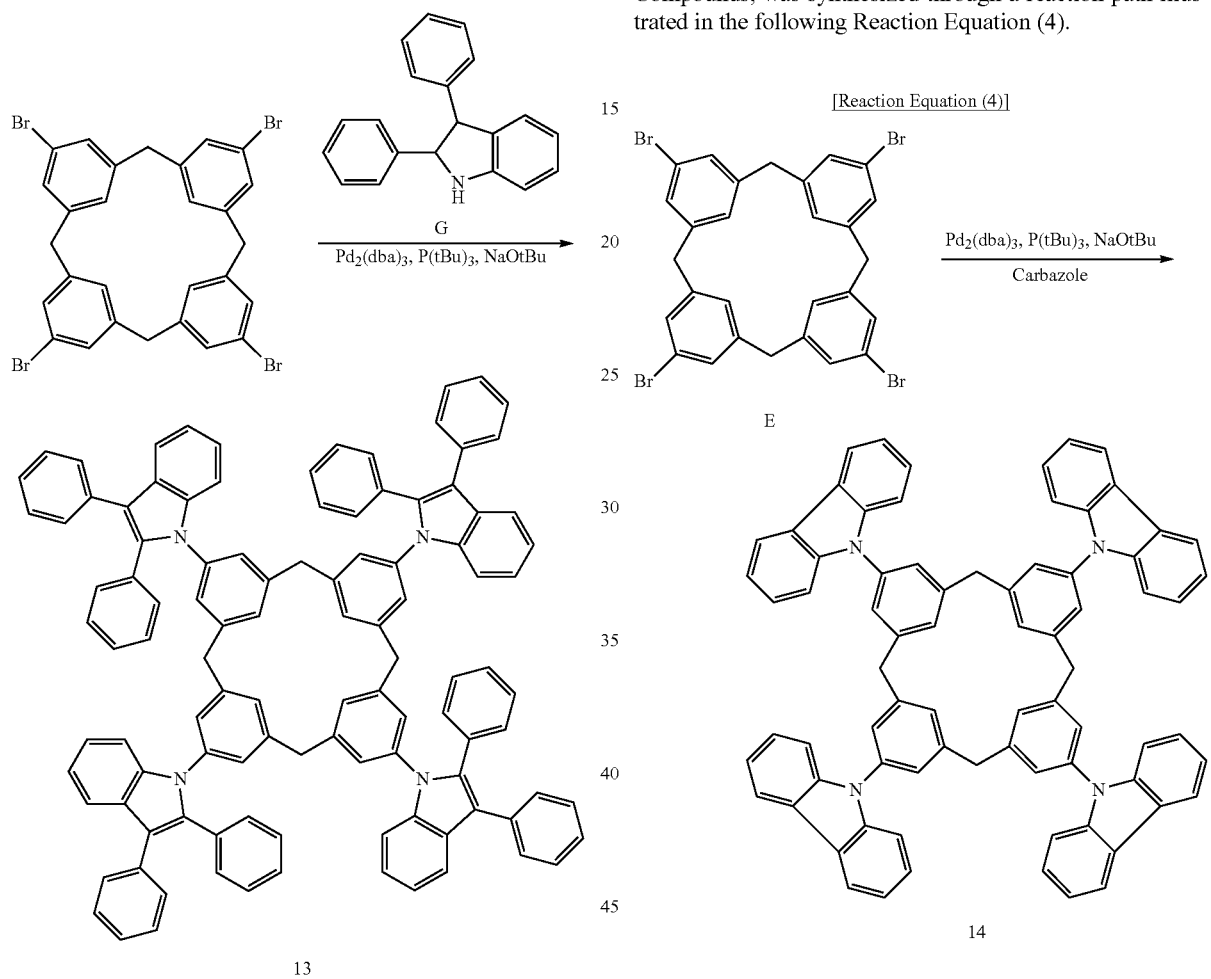

676 mg (1.0 mmol) of Intermediate E, 1.185 mg (4.4 mmol) of Intermediate G, 577 mg (6.0 mmol) of t-BuONa, 46 mg (0.05 mmol) of $Pd_2(dba)_3$ and 10 mg (0.05 mmol) of $P(t-Bu)_3$ were dissolved in 15 mL of toluene and stirred for 3 hours at 90° C. The obtained solution was cooled to a room temperature and extracted three times using distilled water and 20 mL of ethylacetate to obtain an organic layer. The organic layer was dried by magnesium sulfate to vaporize solvent. The resultant residue was separated and purified using a silica gel chromatography to obtain 743 mg of Compound 13 as a white solid form (52% yield). The resultant Compound 13 was detected using HR-MS. A measured value of Compound 13 was 1429.6070 [M+1] and a calculated value based on a chemical formula of Compound 13 ($C_{108}H_{76}N_4$) is 1428.6070.

The resultant Compound 13 was also confirmed using $^1$H-NMR (CDCl$_3$, 300 MHz) to show following peaks represented by δ (ppm): 7.73-7.65 (d, 4H), 7.50 (m, 4H), 7.48-7.41 (m, 12H), 7.39-7.27 (m, 28H), 6.93 (s, 8H), 6.85-6.83 (m, 8H), 6.86 (m, 4H), 3.89 (s, 8H).

Synthetic Example 3

Synthesis of Compound 14

Compound 14, which is one of Examples of Calixarene Compounds, was synthesized through a reaction path illustrated in the following Reaction Equation (4).

676 mg (1.0 mmol) of Intermediate E, 735 mg (4.4 mmol) of carbazole, 577 mg (6.0 mmol) of t-BuONa, 46 mg (0.05 mmol) of $Pd_2(dba)_3$ and 10 mg (0.05 mmol) of $P(t-Bu)_3$ were dissolved in 15 mL of toluene and stirred for 3 hours at 90° C. The obtained solution was cooled to a room temperature and extracted three times using distilled water and 20 mL of ethylacetate to obtain an organic layer. The organic layer was dried by magnesium sulfate to vaporize solvent. The resultant residue was separated and purified using a silica gel chromatography to obtain 694 mg of Compound 14 as a white solid form (68% yield). The resultant Compound 14 was detected using HR-MS. A measured value of Compound 14 was 1021.4192 [M+1] and a calculated value based on a chemical formula of Compound 14 ($C_{26}H_{52}N_4$) is 1020.4192.

The resultant Compound 14 was also confirmed using $^1$H-NMR (CDCl$_3$, 300 MHz) to show following peaks represented by δ (ppm): 8.09 (d, 8H), 7.37-7.28 (m, 16H), 7.23 (dt, 8H), 6.97 (d, 8H), 5.82 (s, 4H), 4.56 (s, 8H).

Synthetic Example 4

Synthesis of Compound 16

Compound 16, which is one of Examples of Calixarene Compounds, was synthesized through a reaction path illustrated in the following Reaction Equation (5).

[Reaction Equation (5)]

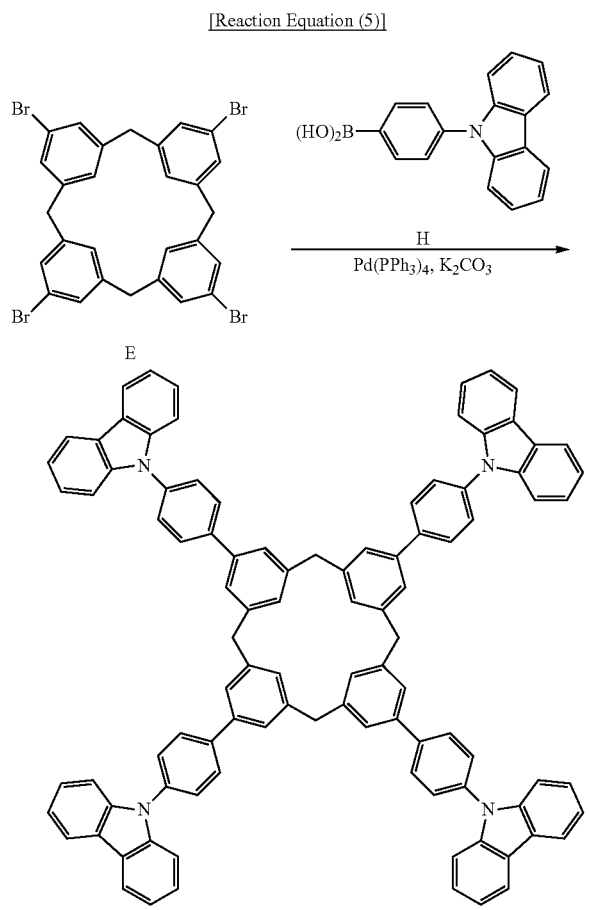

676 mg (1.0 mmol) of Intermediate E, 1.263 mg (4.4 mmol) of Intermediate H, 50 mg (0.05 mmol) of Pd(PPh$_3$)$_4$ and 415 mg (3.0 mmol) of K$_2$CO$_3$ were dissolved in 15 mL of toluene and stirred for 3 hours at 90° C. The obtained solution was cooled to a room temperature and extracted three times using distilled water and 20 mL of ethylacetate to obtain an organic layer. The organic layer was dried by magnesium sulfate to vaporize solvent. The resultant residue was separated and purified using a silica gel chromatography to obtain 610 mg of Compound 16 as a white solid form (46% yield). The resultant Compound 16 was detected using HR-MS. A measured value of Compound 16 was 1325.5444 [M+1] and a calculated value based on a chemical formula of Compound 16 (C$_{100}$H$_{68}$N$_4$) is 1324.5444.

The resultant Compound 16 was also confirmed using $^1$H-NMR (CDCl$_3$, 300 MHz) to show following peaks represented by δ (ppm): 8.12 (m, 4H), 8.10 (m, 4H), 7.49 (m, 4H), 7.44 (m, 4H), 7.41-7.39 (m, 8H), 7.35-7.31 (m, 12H), 7.30-7.26 (m, 10H), 7.22-7.20 (m, 6H), 7.19-7.17 (m, 4H), 7.10 (m, 4H), 4.02 (s, 8H).

Hereinafter, methods of manufacturing the OLED devices illustrated in FIGS. 1 to 5 according to embodiments of the present invention are described.

Referring to FIG. 1, a first electrode 100 may be formed on a substrate (not illustrated). A switching device (not illustrated) may be formed on the substrate to be electrically connected to a data line, a gate line, a power supply, etc., of the OLED device. The switching device may include a thin film transistor (TFT) having a gate electrode, a source electrode, a drain electrode, a semiconductor layer, etc. Alternatively, the switching device may include an oxide semiconductor device having a gate electrode, a gate insulation layer, a source electrode, a drain electrode, a semiconductor oxide active layer, etc.

The first electrode 100 may be electrically connected to the source electrode or the drain electrode of the switching device. The first electrode 100 may be formed using indium tin oxide (ITO), indium zinc oxide (IZO), zinc oxide (ZnOx), gallium oxide (GaOx), tin oxide (SnOx), etc. The first electrode 100 may be formed by a sputtering process, a chemical vapor deposition (CVD) process, a vacuum deposition process, a printing process, etc.

A hole transport layer (HTL) 110 may be formed on the first electrode 100. For example, the HTL 110 may be formed using NPB, TPD, NPD, N-phenylcarbazole, polyvinylcarbazole, etc., by a vacuum deposition process, a thermal deposition process, a spin coating process, etc. The HTL 110 may be formed under proper conditions according to kinds of selected compounds.

An emitting layer (EML) 120 may be formed on the HTL 110 using a host material that includes above-illustrated calixarene compounds and a dopant material. The EML 120 may be formed by a vacuum deposition process, a spin coating process, a printing process, etc. Detailed explanations on the host material are omitted.

The dopant material may include PtOEP, Ir(ppy)$_3$, BTPIr, etc. A doping concentration of the dopant material is not specifically limited. However, the EML 120 may include about 0.01 weight part to about 20 weight part of the dopant material based on a total weight of the host material and the dopant material.

An electron transport layer (ETL) 130 may be formed on the EML 120 using Alq, rubrene, etc. The ETL 130 may be formed by a vacuum process, a thermal deposition process, a spin coating process, a printing process, etc.

A second electrode 140 may be formed on the ETL 130 using a metal such as lithium (Li), magnesium (Mg), aluminium (Al), silver (Ag), etc., or alloys of these metals. The second electrode 140 may be formed by a sputtering process, a CVD process, a vacuum deposition process, a printing process, etc. Accordingly, an OLED device may be provided on the substrate.

Referring to FIG. 2, a hole injection layer (HIL) 105 may be further formed between the first electrode 100 and the HTL 110, and an electron injection layer (EIL) 135 may be further formed between the ETL 130 and the second electrode 140.

The HIL 105 may be formed on the first electrode 100 using TCTA, m-MTDATA, m-MTDAPB, 2-TNATA, etc., by a vacuum process, a thermal deposition process, a spin coating process, a printing process, etc.

The EIL 135 may be formed on the ETL 130 using LiF, NaCl, CsF, Li$_2$O, BaO by a vacuum process, a thermal deposition process, a spin coating process, a printing process, etc.

Referring to FIG. 3, a hole blocking layer (HBL) 125 may be further formed between the EML 120 and the ETL 130.

The HBL 125 may be formed on the EML 120 using BCP, TAZ, etc., by a vacuum process, a thermal deposition process, a spin coating process, a printing process, etc.

Referring to FIG. 4, an electron blocking layer (EBL) 115 may be further formed between the HTL 110 and the EML 120. The EBL 115 may be formed using a material that has a substantially low electron-transporting capability such as Ir(ppz)$_3$. The EBL 115 may be formed by a vacuum process, a thermal deposition process, a spin coating process, a printing process, etc.

Referring to FIG. 5, the OLED device may include both of the HBL 125 and the EBL 115.

Hereinafter, experimental results of Examples and Comparative Examples evaluating luminance characteristics of the OLED devices are described.

Example 1

An ITO substrate manufactured by Corning. Co., LTD. was cut by a dimension of 50 mm×50 mm×0.7 mm to prepare a first electrode (an anode). The ITO substrate has a sheet resistance of 15 Ω/cm². The ITO substrate was cleaned using an ultrasonic wave in pure water and isopropyl alcohol for 5 minutes. Subsequently, the ITO substrate was exposed to UV light for about 30 minutes, and then cleaned by ozone. The ITO substrate was then loaded in a vacuum deposition apparatus.

A HIL was formed on the ITO substrate by depositing 2-TNATA and a HTL was formed on the HIL by depositing NPB. The thickness of the HIL and HTL was about 600 Å and 300 Å, respectively.

An EML was formed on the HTL by depositing host and dopant materials to have a thickness of about 300 Å. Compound 14 of the above Examples of Calixarene Compounds was used as a phosphorescent host material and Ir(ppy)$_3$ was used as a green phosphorescent dopant material. The weight ratio of the host and dopant materials was about 93:7.

An ETL was formed on the EML by depositing Alq3 to have a thickness of about 300 Å. An EIL was formed on the ETL by depositing LiF to have a thickness of about 10 Å. A second electrode (a cathode) was formed on the EIL by depositing Al to have a thickness of about 3,000 Å. Accordingly, an OLED device was manufactured.

Example 2

An ITO substrate manufactured by Corning. Co., LTD. was cut by a dimension of 50 mm×50 mm×0.7 mm to prepare a first electrode (an anode). The ITO substrate has a sheet resistance of 15 Ω/cm². The ITO substrate was cleaned using an ultrasonic wave in pure water and isopropyl alcohol for 5 minutes. Subsequently, the ITO substrate was exposed to UV light for about 30 minutes, and then cleaned by ozone. The ITO substrate was then loaded in a vacuum deposition apparatus.

A HIL was formed on the ITO substrate by depositing 2-TNATA and a HTL was formed on the HIL by depositing NPB. The thickness of the HIL and HTL was about 600 Å and 300 Å, respectively.

An EML was formed on the HTL by depositing host and dopant materials to have a thickness of about 300 Å. Compound 16 of the above Examples of Calixarene Compounds was used as a phosphorescent host material and BTPIr was used as a red phosphorescent dopant material. The weight ratio of the host and dopant materials was about 90:10.

An ETL was formed on the EML by depositing Alq3 to have a thickness of about 300 Å. An EIL was formed on the ETL by depositing LiF to have a thickness of about 10 Å. A second electrode (a cathode) was formed on the EIL by depositing Al to have a thickness of about 3,000 Å. Accordingly, an OLED device was manufactured.

Comparative Example 1

An OLED device was manufactured by performing processes substantially the same as those in Example 1 except for the host material in an EML. CBP was used as a phosphorescent host material instead of Compound 14 in Example 1.

Comparative Example 2

An OLED device was manufactured by performing processes substantially the same as those in Example 2 except for the host material in an EML. CBP was used as a phosphorescent host material instead of Compound 16 in Example 2.

Current density, color coordinates, brightness and luminance efficiency of the OLED devices in Example 1, Example 2, Comparative Example 1 and Comparative Example 2 were measured, respectively, and the results are shown in following Table 1.

TABLE 1

| | Current Density (mA/cm², at 6 V) | Color Coordinate | Brightness (cd/m²) | Luminance Efficiency (cd/A) |
|---|---|---|---|---|
| Example 1 | 21.46 | (0.32, 0.65) | 3,620 | 16.87 |
| Example 2 | 20.75 | (0.63, 0.37) | 2,314 | 11.15 |
| Comparative Example 1 | 11.17 | (0.30, 0.60) | 1,268 | 11.35 |
| Comparative Example 2 | 14.27 | (0.62, 0.38) | 1,023.3 | 7.17 |

As shown in Table 1, the OLED devices of Examples 1 and 2 using Compound 14 and Compound 16, both of which are calixarene compounds, as the phosphorescent host materials exhibited high current density relative to those of Comparative Examples 1 and 2 at the same voltage. Thus, the driving voltage of the OLED devices may be reduced so that the OLED devices may have extended life-time. Further, the OLED devices of Examples 1 and 2 also exhibited high brightness and luminance efficiency relative to those of Comparative Examples 1 and 2. Thus, it can be noted that the charge-transporting capability in the EMLs of the OLED devices may be increased.

Although a few example embodiments of the present invention have been described, those skilled in the art will readily appreciate that many modifications are possible in the example embodiments without materially departing from the novel teachings and advantages of the present invention. Accordingly, all such modifications are intended to be included within the scope of the invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific example embodiments disclosed, and that modifications to the disclosed example embodiments, as well as other example embodiments, are intended to be included within the scope of the appended claims of the present invention. The present invention is defined by the following claims, with equivalents of the claims to be included therein.

What is claimed is:

1. An organic light emitting display device, comprising:

a first electrode;

a hole transport layer, an emitting layer and an electron transport layer disposed sequentially on the first electrode; and a second electrode formed on the electron transport layer, wherein the emitting layer comprises a host material comprising a calixarene compound represented by Chemical Formula (1) and a dopant material,

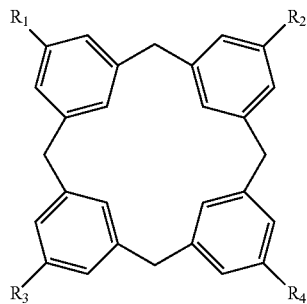

Chemical Formula (1)

wherein, in the Chemical Formula (1), each of $R_1$ to $R_4$ independently represents one selected from the group consisting of a phenyl group, a biphenyl group, a naphthyl group, an anthracene group, a phenanthrene group, a pyrene group and a benzopyrene group which are unsubstituted or substituted with an aromatic group, an indole group or an indole group substituted with an aryl group, or a phenyl group substituted with 9-carbazole.

2. The organic light emitting display device of claim 1, wherein the host material comprises at least one calixarene compound selected from the compounds represented by Chemical Formula (2), Chemical Formula (3), Chemical Formula (4) and Chemical Formula (5)

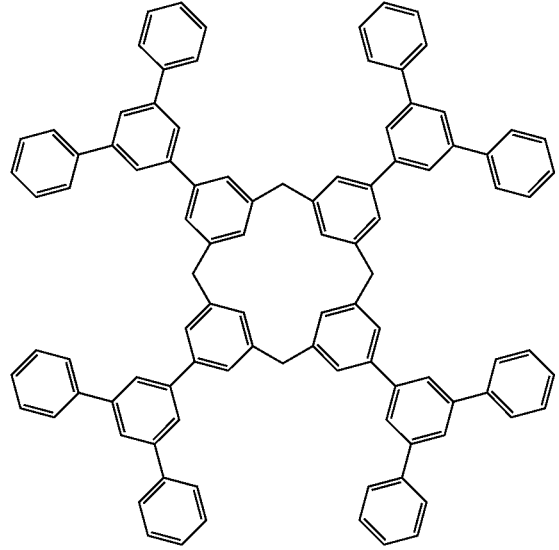

Chemical Formula (2)

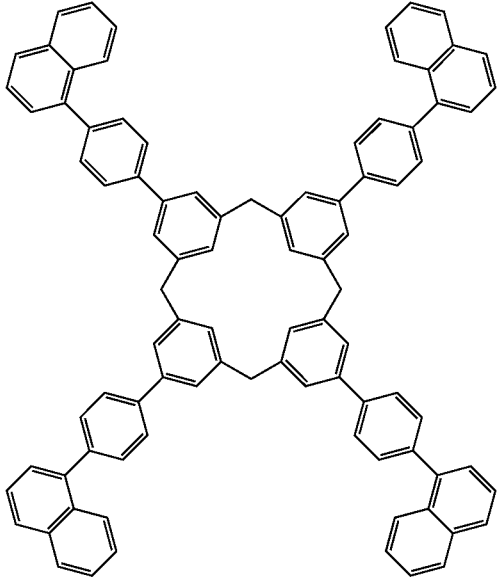

Chemical Formula (3)

Chemical Formula (4)
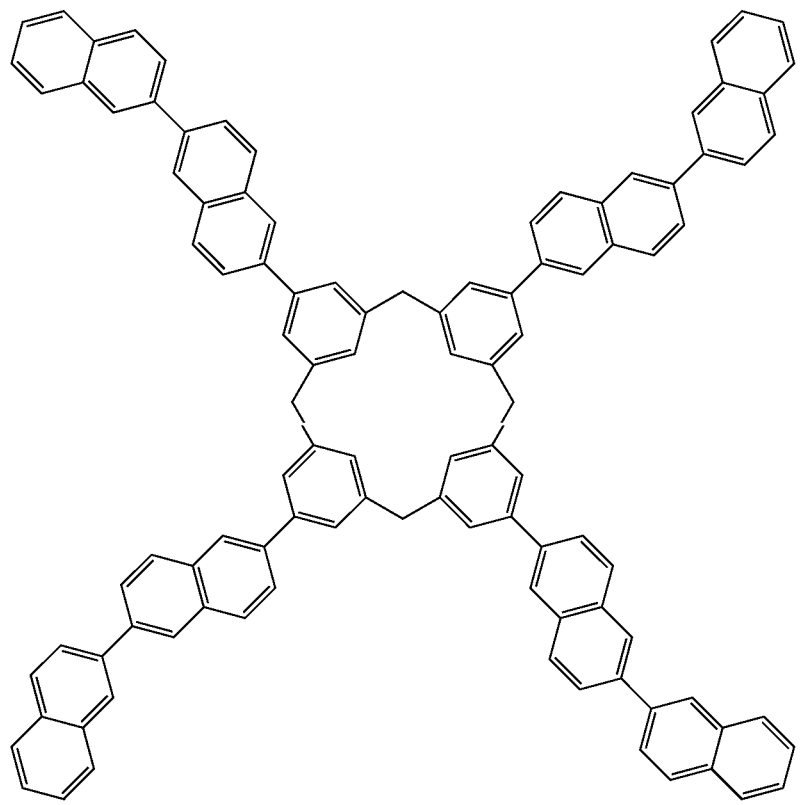
Chemical Formula (5)
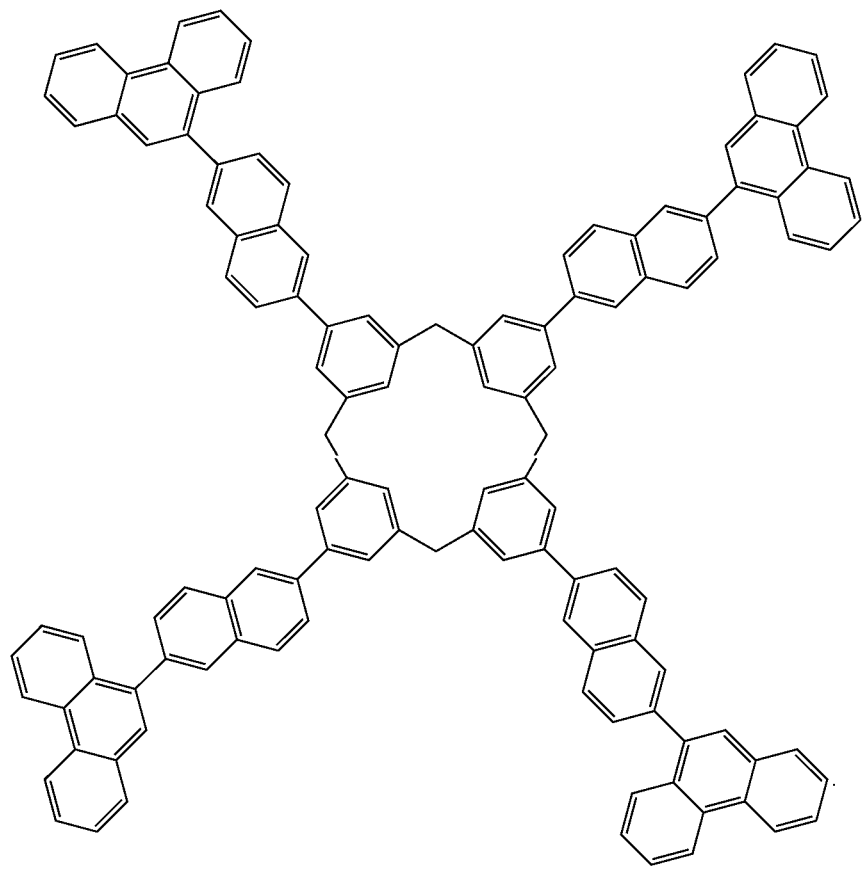

3. The organic light emitting display device of claim 1, wherein the host material comprises a calixarene compound represented by Chemical Formula (6)

Chemical Formula (6)

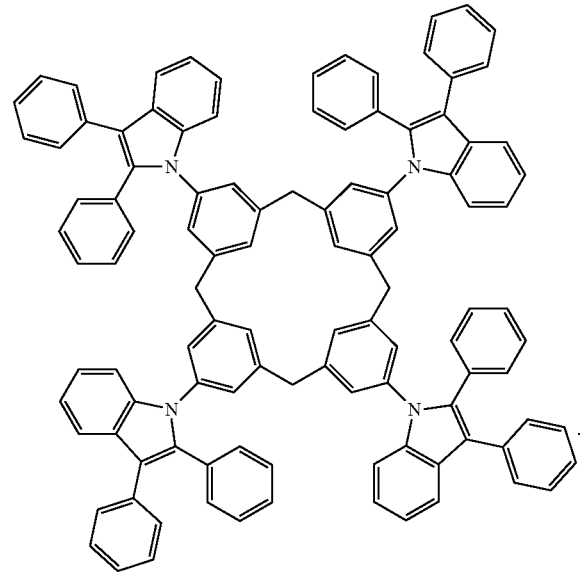

4. The organic light emitting display device of claim 1, the host material comprises at least one calixarene compound selected from the compounds represented by Chemical Formula (7), Chemical Formula (8) and Chemical Formula (9)

Chemical Formula (7)

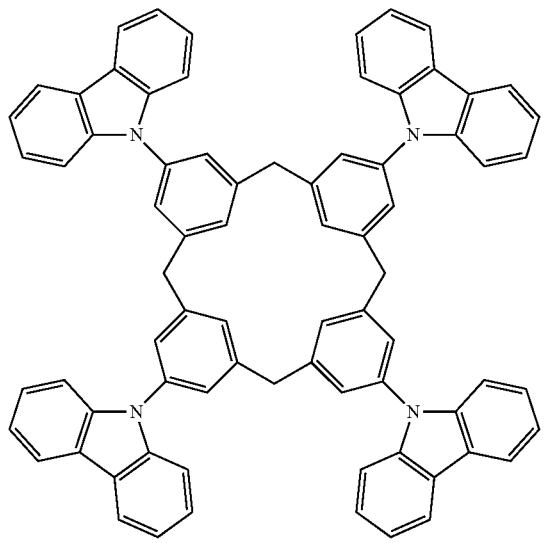

Chemical Formula (8)

Chemical Formula (9)

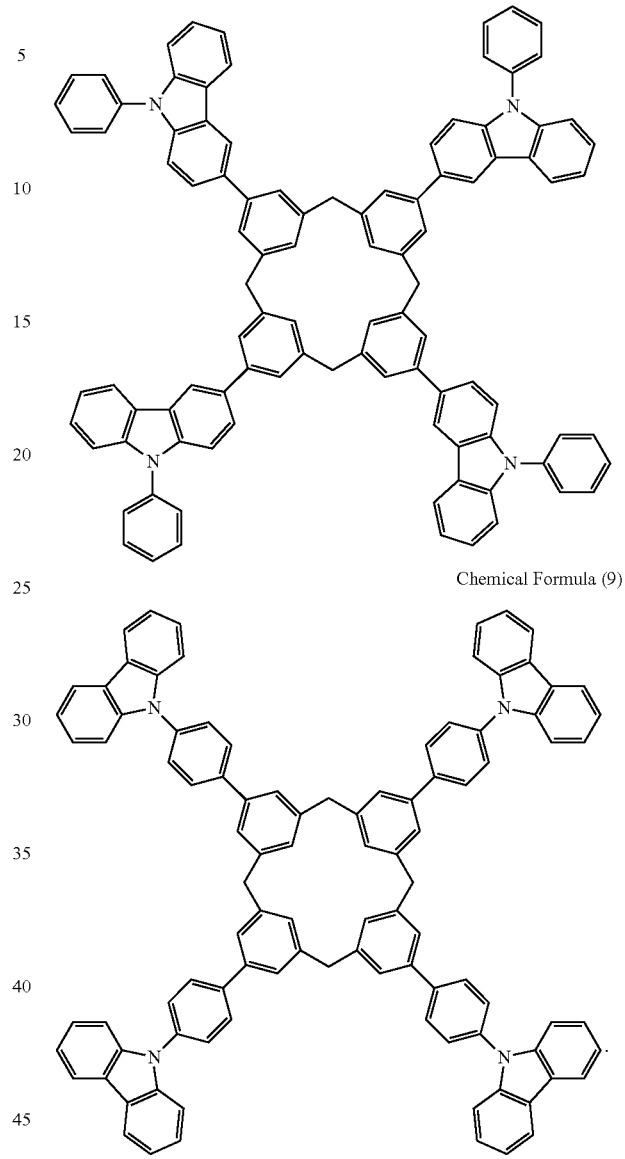

5. The organic light emitting display device of claim 1, wherein the dopant material comprises at least one organometallic compound having a metal selected from the group consisting of iridium (Ir), platinum (Pt), osmium (Os) and gold (Au).

6. The organic light emitting display device of claim 1, wherein the dopant material comprises at least one selected from the group consisting of PtOEP, Ir(ppy)$_3$ and BTPIr.

7. The organic light emitting display device of claim 1, further comprising a hole injection layer formed between the first electrode and the hole transport layer.

8. The organic light emitting display device of claim 1, further comprising an electron injection layer formed between the electron transport layer and the second electrode.

9. The organic light emitting display device of claim 1, further comprising a hole blocking layer formed between the emitting layer and the electron transport layer.

10. The organic light emitting display device of claim 1, further comprising an electron blocking layer formed between the emitting layer and the hole transport layer.

11. The organic light emitting display device of claim 1, further comprising a switching device electrically connected to the first electrode, wherein the first electrode is electrically connected to a source electrode or a drain electrode of the switching device and the first electrode serves as an anode providing holes.

12. The organic light emitting display device of claim 1, wherein the host material serves as a fluorescent host material or phosphorescent host material, and the dopant material includes a fluorescent dopant material or a phosphorescent dopant material.

13. A method for manufacturing an organic light emitting display device, comprising:
preparing a substrate having a switching device;
forming a first electrode on the substrate;
forming a hole transport layer, an emitting layer and an electron transport layer sequentially on the first electrode; and
forming a second electrode on the electron transport layer, wherein the emitting layer is formed using a host material comprising a calixarene compound represented by Chemical Formula (1) and a dopant material,

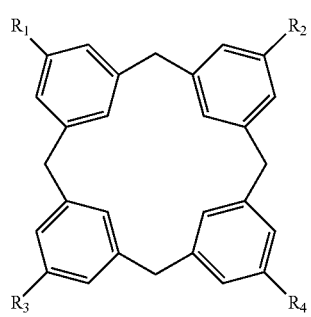

Chemical Formula (1)

wherein, in the Chemical Formula (1), each of $R_1$ to $R_4$ independently represents one selected from the group consisting of a phenyl group, a biphenyl group, a naphthyl group, an anthracene group, a phenanthrene group, a pyrene group and a benzopyrene group which are unsubstituted or substituted with an aromatic group, an indole group or an indole group substituted with an aryl group, or a phenyl group substituted with 9-carbazole.

14. The method for manufacturing an organic light emitting display device of claim 13, further comprising:

forming a hole injection layer on the first electrode prior to forming the hole transport layer; and forming an electron injection layer on the electron transport layer prior to forming the second electrode.

15. The method for manufacturing an organic light emitting display device of claim 13, further comprising:

forming an electron blocking layer on the hole transport layer prior to forming the emitting layer; and forming a hole blocking layer on the emitting layer after forming the emitting layer.

* * * * *